(12) United States Patent
Yang et al.

(10) Patent No.: US 8,609,851 B2
(45) Date of Patent: Dec. 17, 2013

(54) NITROPYRIDINYL ETHYLENEIMINE COMPOUND, THE PHARMACEUTICAL COMPOSITION CONTAINING IT, THE PREPARATION METHOD AND USE THEREOF

(75) Inventors: Shangjin Yang, Beijing (CN); Jianhui Yan, Beijing (CN); Ligang Wang, Beijing (CN); Xingna Guo, Beijing (CN); Shubin Li, Beijing (CN); Guoqiang Wu, Beijing (CN); Ruiya Zuo, Beijing (CN); Xin Huang, Beijing (CN); Hongtao Wang, Beijing (CN); Lingling Wang, Beijing (CN); Wenjuan Huang, Beijing (CN); Huigang Lu, Beijing (CN); Ke Feng, Beijing (CN); Fang Li, Beijing (CN); Huimin He, Beijing (CN); Yu Liu, Beijing (CN)

(73) Assignee: Beijing Yiling Bioengineering Co., Ltd., Beijing (CN)

( * ) Notice: Subject to any disclaimer, the term of this patent is extended or adjusted under 35 U.S.C. 154(b) by 62 days.

(21) Appl. No.: 13/126,907

(22) PCT Filed: Oct. 27, 2009

(86) PCT No.: PCT/CN2009/074639
§ 371 (c)(1),
(2), (4) Date: Apr. 29, 2011

(87) PCT Pub. No.: WO2010/048880
PCT Pub. Date: May 6, 2010

(65) Prior Publication Data
US 2012/0071515 A1    Mar. 22, 2012

(30) Foreign Application Priority Data
Oct. 31, 2008    (CN) .......................... 2008 1 0173259

(51) Int. Cl.
*C07D 401/00*     (2006.01)
(52) U.S. Cl.
USPC ..................................................... 546/268.1
(58) Field of Classification Search
USPC ..................................................... 546/268.1
See application file for complete search history.

(56) References Cited

U.S. PATENT DOCUMENTS 6,310,237 B1    10/2001    Feng et al.

FOREIGN PATENT DOCUMENTS

| CN | 200380102812.7 | 12/2005 |
| WO | WO 88/07379 | 10/1988 |
| WO | WO 2004/033415 A1 | 4/2004 |
| WO | WO 2005/042471 A1 | 5/2005 |

OTHER PUBLICATIONS

Wermuth, "Molecular Variations Based on Isosteric. Replacements," "The Practice of Medicinal Chemistry," 1996, pp. 203-237.*
Khan et al., Tumor growth inhibitory nitrophenylziridines and related compounds: structure-activity relationship, Chemico-Biological Interactions, vol. 1, No. 1, 1969, pp. 27-47.
Extended European Search Report dated Apr. 5, 2012 for European Application No. 09823072.5.
*Retroviral-mediated gene therapy for treatment of hepatocellular carcinoma: An innovative approach for cancer therapy.* Proc. Natl. Acad. Sci, USA, vol. 88 pp. 8039-8043, Sep. 1991. Medical Sciences. Brian E. Huber; Cynthia A. Richards; and Thomas A. Krenitsky. Division of Experimental Therapy, Wellcome Research Laboratories, Research Triangle Park, NC.
*Selective cell ablation in the mammary gland of transgenic mice.* Endocrine-Related Cancer, 1997 4: 67-74. B. Gusterson[1]; W. Cui; M. Iwobi[1]; M.R. Crompton[1]; G. Harold; S. Hobbs[2]; T. Kamalati[1]; R. Knox[2]; C. Neil; F. Yull; B. Howard[1]; and A. J. Clark. Division of Molecular Biology, Roslin Institute, Roslin, Midlothian, UK; [1]Section of Cell Biology and Experimental Pathology and [2]CRC Centre for Cancer Therapeutics, Institute of Cancer Research, Haddow Laboratories, Sutton, Surrey, UK.
*The bioactivation of CB 1954 and its use as a prodrug in antibody-directed enzyme prodrug therapy (ADEPT)* Cancer and Metastasis Reviews 12: 195-212, 1993. Richard J. Knox; Frank Friedlos and Marion P. Boland. Molecular Pharmacology Unit, Section of Drug Development, Institute of Cancer Research, Sutton, Surrey, UK.
*Mustard Prodrugs for Activation by Escherichia coli Nitroreductase in Gene-Directed Enzyme Prodrug Therapy.* Journal of Med. Chem. 1997, vol. 40: 1270-1275. Frank Friedlos; William A. Denny[†]; Brian D. Palmer[554]; and Caroline J. Springer[554]. Cancer Research Campaign Centre for Cancer Therapeutics, Institute of Cancer Research, Sutton, Surrey, UK; and Cancer Society Research Laboratory, Faculty of Medicine and Health Sciences, The University of Auckland, Auckland, New Zealand.

(Continued)

*Primary Examiner* — Shirley V Gembeh
(74) *Attorney, Agent, or Firm* — Knobbe Martens Olsen & Bear LLP

(57) ABSTRACT

The present invention discloses a nitropyridinyl ethyleneimine compound as shown in the formula I and a preparation method of the same, as well as use of the compound in manufacture of a prodrug and in manufacture of a drug for treating a tumor.

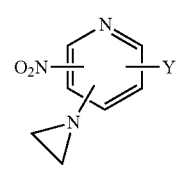

I

8 Claims, No Drawings

(56) References Cited

OTHER PUBLICATIONS

*The Preparation of 3-Fluoroisonicotinic Acid and Related Compounds.* J. Org. Chem. 1955, vol. 20: 1729-1731. Arthur Roe and Robert B. Seligman[1]. Contribution from the Venable Chemistry Laboratory of the University of North Carolina.

*The Preparation of 5-Fluoronicotinic Acid and 5-Fluoronicotinamide*[1]. J. Org. Chem. 1949, vol. 14: 328-332. G. F. Hawkins and Arthur Roe. Contribution from the Venable Chemistry Laboratory of the University of North Carolina.

*Substituent Effects on the Decarboxylation of Dinitrobenzoate Ions, Representative Aromatic $S_E^1$ Reactions*[1]. . J. Org. Chem. 1985, vol. 50, 1041-1045. Pascual Segura [2]; Joseph F. Bennett; and Laura Villanova. University of California, Santa Cruz, California.

Antimalarial 2-Alkoxy-6-chloro-9-dialkylaminoalkylamino-1: 10-diaza-anthracenes. *J. Chem. Soc.* 1954, 2448-2455. D. M. Besly and A. A. Goldberg.

International Search Report for PCT/CN2009/074639—Mailed Jan. 7, 2010.

\* cited by examiner

NITROPYRIDINYL ETHYLENEIMINE COMPOUND, THE PHARMACEUTICAL COMPOSITION CONTAINING IT, THE PREPARATION METHOD AND USE THEREOF

FIELD OF THE INVENTION

The invention relates to a novel nitropyridine compound and use thereof; particularly to a novel nitropyridinyl ethyleneimine compound, a preparation method for the same and use of the compound in manufacture of a prodrug for use in combination of the nitroreductase-mediated gene-directed enzyme prodrug therapy (GDEPT) with cell ablation therapy, as well as in manufacture of a drug for treating tumors.

BACKGROUND TECHNIQUES

A tumor-selective prodrug can be selectively converted in vivo into a more active compound and kills locally tumor cell, which can avoid the side-effect on human body resulted from systematic or topically direct administration. Thus, it has a considerably excellent prospect for treating tumors.

Due to disordering of their proliferation, most of malignant tumors always generate a hypoxic region which is resistant to both radiation therapy and chemical medicine therapy, and some time the treatment fails due to further development of the tumors; and since the normal tissues in the human body have abundant oxygen, the hypoxia is chosen as a physiological characteristics targeting to tumors. A hypoxia-activated prodrug makes use of the said physiological characteristics of the tumors, that is, a non-toxic prodrug can be activated into a toxic compound under a hypoxic environment by a particular enzyme, thus attaining an anti-tumor effect.

Therapies in which a non-toxic drug is converted into a toxic drug include "antibody-directed enzyme prodrug therapy (ADEPT)", "gene-directed enzyme prodrug therapy (GDEPT)", "virus-directed enzyme prodrug therapy" (VDEPT), or "cell ablation therapy". Among them, the "antibody-directed enzyme prodrug therapy (ADEPT)" was disclosed in WO88/07379; the "gene-directed enzyme prodrug therapy (GDEPT)" was disclosed in U.S. Pat. No. 6,310,237; the "virus-directed enzyme prodrug therapy (VDEPT)" was published in Proc. Natl. Acad. Sci. USA (1991) 88, 8039; and the "cell ablation therapy" was published in Endocrine Related Cancer, 1997, 4, 67-74.

Since nitroaromatic compounds could be reduced by a flavin-protease existed in mammalian and in bacteria to achieve gradual addition of up to six electrons, while a major enzymatically metabolized product is typically a four-electrons-containing adduct (hydroxylamine), so the nitroaromatic compound may serve as a prodrug in the various therapies mentioned above.

Knox, et al. [Cancer Med Rev., 1993, 12, 195] and Friedlos, et al. [J. Met. Chem., 1997, 40, 1270] reports that dinitrobenzamide ethyleneimine and nitro or dinitrobenzamide nitrogen mustards serve as a substrate for a nitroreductase (NTR) of the aerobic *Escherichia coli*, and also serve as a specific prodrug in combination with the NTR's GDEPT.

CN200380102812.7 discloses a cytotoxic and nitroaniline-based asymmetric nitrogen mustard as a prodrug, which is usable as a nitroreductase, especially the nitroreductase encoded by *E. coli* nsfB gene or by *Clostridium* species in the GDEPT and cell ablation therapy.

However, there is still a need for developing a novel nitroaromatic compound for treating tumors, which is capable of acting as a prodrug in the above therapies.

DISCLOSURE OF THE INVENTION

The present invention provides a novel nitropyridinyl ethyleneimine compound, a preparation method for the same and use thereof in manufacture of a prodrug for use in combination of the nitroreductase-mediated "gene-directed enzyme prodrug therapy" with "cell ablation therapy", as well as in manufacture of a drug for treating tumors.

The present invention firstly provides a nitropyridinyl ethyleneimine compound as shown in general formula (I) or its pharmaceutically acceptable salts:

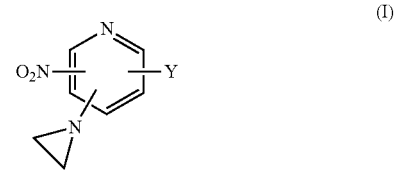

(I)

Wherein,

Y is —NHCOR, $CONRCO_2R^2$, CONR morpholine, CONHR, $CONRR^2$, $CONHOR^2$, $CONHSO_2R$, $SO_2NH_2$—, $SO_2NHR$— or $SO_2NRR^2$; in which R and $R^2$ represent independently from each other H, hydroxyl, or $C_{1-6}$ lower alkyl group which is optionally substituted with one or more hydroxyl groups and/or one or more amino groups;

Said pharmaceutically acceptable salts thereof are salts resulted from addition with an acid or with an alkali; said acid is selected from the group consisting of hydrogen chloride, sulphuric acid, phosphoric acid, acetic acid, citric acid, oxalic acid, malonic acid, salicylic acid, malic acid, fumaric acid, succinic acid, ascorbic acid, maleic acid, methane sulfonic acid or isethionic acid; said alkali is selected from the group consisting of sodium carbonate, potassium carbonate, sodium hydroxide, potassium hydroxide, ammonia, triethylamine or triethanolamine.

Preferably nitropyridinyl ethyleneimine compounds of the present invention are:

2-(1-ethyleneimine)-4-carbamoyl-3-nitropyridine as shown in the formula II or pharmaceutically acceptable salts thereof

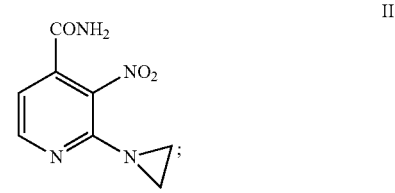 [SMILES: NC(=O)c1ccnc(N2CC2)c1[N+](=O)[O-]]

II 2-(1-ethyleneimine)-5-carbamoyl-3-nitropyridine as shown in the formula III or pharmaceutically acceptable salts thereof

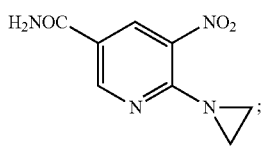

2-(1-ethyleneimine)-3-carbamoyl-5-nitropyridine as shown in the formula IV or pharmaceutically acceptable salts thereof

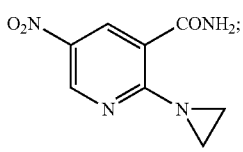

2-(1-ethyleneimine)-6-carbamoyl-3-nitropyridine as shown in the formula V or pharmaceutically acceptable salts thereof

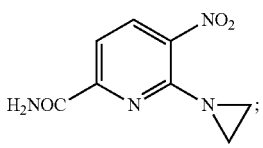

or
2-(1-ethyleneimine)-4-carbamoyl-5-nitropyridine as shown in the formula VI or pharmaceutically acceptable salts thereof

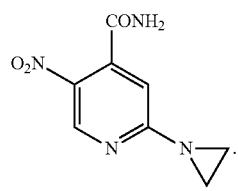

wherein physical and chemical properties of the compounds of formula II-VI set forth in the Present invention are given as follows:

| No | Mp (° C.) | Molecular Formula | Element Assay |
|---|---|---|---|
| II | 170 (decomposed) | C8H8N4O3 | C, H, N |
| III | 150 (decomposed) | C8H8N4O3 | C, H, N |
| IV | 160 (decomposed) | C8H8N4O3 | C, H, N |
| V | 170 (decomposed) | C8H8N4O3 | C, H, N |
| VI | 170 (decomposed) | C8H8N4O3 | C, H, N |

Wherein the pharmaceutically acceptable salts of any one of the compounds as shown in the formula II-VI are salts resulted from addition with a pharmaceutically acceptable acid or an alkali, said acid is selected from the group consisting of hydrogen chloride, sulphuric acid, phosphoric acid, acetic acid, citric acid, oxalic acid, malonic acid, salicylic acid, malic acid, fumaric acid, succinic acid, ascorbic acid, maleic acid, methane sulfonic acid, or isethionic acid; said alkali is selected from the group consisting of sodium carbonate, potassium carbonate, sodium hydroxide, potassium hydroxide, ammonia, triethylamine, or triethanolamine.

The present invention provides a method for preparation of the nitropyridinyl ethyleneimine compound as shown in the general formula (I) or its pharmaceutically acceptable salts:

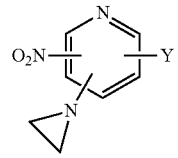

Wherein:
Y represents OR, NHCOR, CONRCO$_2$R$^2$, CONR-morpholine, CONHR, CONRR$^2$, CONHOR$^2$, CONHSO$_2$R, SO$_2$NH$_2$—, SO$_2$NHR— or SO$_2$NRR$^2$, in which R and R$^2$ are independently from each other H, hydroxyl, or C$_{1-6}$ lower alkyl group which may be optionally substituted with one or more hydroxyl groups and/or one or more amino groups.

The preparation method set forth in the present invention comprises the following steps:

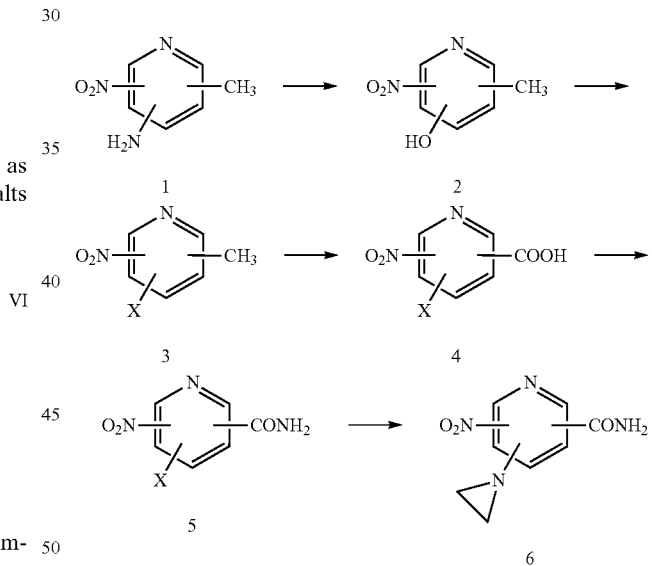

a) A compound as shown in the formula 1 is diazotized under the action of a nitrite so that the amino group in the compound of the formula 1 is converted into a phenolic hydroxyl group, yielding a compound as shown in the formula 2;

b) A compound as shown in the formula 2 is reacted at elevated temperature with a phosphorus halide, halogenated sulfoxide, organic acyl halide, or sulfonyl halide to give a compound as shown in the formula 3, wherein X in the compound of the formula 3 is a halogen or OSO$_2$R$^1$ in which R$^1$ is C$_{1-6}$ aliphatic group, C$_{3-6}$ saturated cyclic substituent, or an aromatic group;

it is preferred that the compound of the invention as shown in the formula 2 is reacted at elevated temperature with a phosphorus oxychloride, phosphorus tribromide, or sulfonyl halide to give a compound shown in the formula 3, wherein X in the compound as shown in the formula 3 is Cl, Br, or $OSO_2R^1$ in which $R^1$ is $C_{1-6}$ aliphatic group, $C_{3-6}$ saturated cyclic substituent, or aromatic group;

c) The methyl group in the compound of formula 3 is oxidized into a carboxyl group under the action of a dichromate, giving a compound of formula 4; also in the present invention, the methyl group in the compound of the formula 3 can also be oxidized into carboxyl group using other conventional oxidants known in the art.

d) The carboxyl group in the compound of formula 4 is converted into an acyl group under the action of $SOCl_2$ and an amine, yielding a compound of formula 5; the carboxyl group in the compound of formula 4 could also be converted into an acyl group using other conventional acylating agents known in the art.

e) The compound of the formula 5 is reacted with ethyleneimine in an organic solvent at 20-25° C. for 10 min-48 h to yield a compound of the formula 6, wherein the organic solvent is a solvent capable of dissolving the reactants, for example, including but not limited to ethyl acetate.

The preparation of the pharmaceutically acceptable salts of the nitropyridinyl ethyleneimine compound as shown in the formula I includes the step of reacting the compound I with the corresponding acid or alkali under agitation in an organic solvent, for example, alcoholic solvents.

The present invention also provides use of the nitropyridinyl ethyleneimine compound of the formula I or pharmaceutically acceptable salts thereof in preparation of a prodrug, in which the nitropyridinyl ethyleneimine compound of the formula I of the present invention or its pharmaceutically acceptable salt thereof acts as a hypoxia-selective cytotoxin.

Furthermore, the present invention also provides use of the nitropyridinyl ethyleneimine compound of the formula I or pharmaceutically acceptable salts thereof in preparation of a drug for treating tumors, in which the nitropyridinyl ethyleneimine compound of the formula I of the present invention or the pharmaceutically accepted salt thereof serves as a prodrug useful in "gene-directed enzyme prodrug therapy" (GDEPT). The term "gene-directed enzyme prodrug therapy (GDEPT)" includes treating both viral- and non-viral delivery system; and this term refers not only to the "gene-directed enzyme prodrug therapy (GDEPT)", but also to the "anti-body-directed enzyme prodrug therapy (ADEPT)" and the "virus-directed enzyme prodrug therapy (VDEPT)".

In the use in preparation of the drug for treating tumors as described in the present invention, it is preferred that any one of the nitropyridinyl ethyleneimine compounds shown in the formula II-VI or the pharmaceutically acceptable salts thereof serves as prodrugs in the "gene-directed enzyme prodrug therapy (GDEPT)".

In the use of the compound shown in the formula I of the present invention or the pharmaceutically acceptable salts thereof in preparation of the drug for treating tumors, the compound shown in the formula I, preferably any one of the nitropyridinyl ethyleneimine compounds shown in the formula II-VI or the pharmaceutically acceptable salts thereof, can be used in combination with at least one nitroreductase; and the nitroreductase can be encoded by the *E. coli* nfs B gene or the *Clostridium* species.

In the use of the compound shown in the formula I of the present invention or pharmaceutically acceptable salts thereof in preparation of the drug for treating tumors, a therapeutically effective amount of the compound of the formula I, preferably any one of the nitropyridinyl ethyleneimine compounds shown in the formula II-VI, or a mixture thereof, or the pharmaceutically acceptable salts thereof, can be administrated as a prodrug useful in the "gene-directed enzyme prodrug therapy (GDEPT)" to tumor cells of a subject in need thereof.

In the use in preparation of the drug for treating tumors as described in the present invention, the nitropyridinyl ethyleneimine compounds shown in the formula I of the present invention or the pharmaceutically acceptable salts thereof serve also as a prodrug useful in "cell ablation therapy", wherein the compound shown in the formula I of the present invention, preferably any one of the compounds shown in the formula II-VI or the pharmaceutically acceptable salts thereof, can be used in combination with at least one nitroreductase; and the nitroreductase can be encoded by the *E. coli* nfs B gene or the *Clostridium* species. In the use of the compound shown in the formula I of the present invention or the pharmaceutically acceptable salts thereof in preparation of the drug for treating tumors, a therapeutically effective amount of the compound of the formula I, preferably any one of the nitropyridinyl ethyleneimine compounds shown in the formula II-VI, or a mixture, or the pharmaceutically acceptable salts thereof, can be administrated as a prodrug useful in cell ablation therapy to tumor cells in tissues of an subject, in order to ablate tumor cells in the subject's tissues, in the issues at least one nitroreductase is expressed.

The present invention also provides a pharmaceutical composition of the compound shown in the formula I of the present invention, the composition comprises a therapeutically effective amount of the compound of formula I, preferably any one of the compounds shown in the formula II-VI, or a mixture thereof, or the pharmaceutically acceptable salt thereof, and a pharmaceutically acceptable carrier, in which the carrier may be one or more of pharmaceutically acceptable excipients, adjuvants, buffers, and stabilizers. The pharmaceutically acceptable excipient, adjuvant, buffer, or stabilizers should be preferably non-toxic and have no interference on the function of the active ingredient. Choice of the specific kinds of the carrier should be dependent on the route of administration which may be oral administration or injection, such as subcutaneous or intravenous injection. It may be understood that these factors could be easily determined by those skilled in the art without additional experiments.

The pharmaceutical composition of the present invention can be formulated into various pharmaceutical dosage forms using conventional techniques in the art, such as tablets, capsules, powders or liquids for oral administration. The tablet may comprises a solid carrier or adjuvant; the capsule may comprise a solid carrier, such as gelatin; the liquid formulation typically comprises a liquid vehicle such as water, animal- or vegetable oils, mineral or synthetic oils; may comprise a physiological saline, the solution of glucose or of other saccchrides, or diols such as ethylene glycol, propylene glycol, or polyethylene glycol.

When the pharmaceutical composition of the present invention is formulated into pharmaceutical dosage form suitable for intravenous or subcutaneous administration by those skilled in the art using conventional techniques, it can be formulated into a pyrogen-free solution formulation with an appropriate pH value, isotonicity, and stability. For example, such isotonic vehicle as sodium chloride injection, Ringer's injection, or Lactated Ringer's injection could be used. If desired, the solution formulation can also comprise one or more of preservatives, stabilizers, buffers, and antioxidants, and it can also comprise other additives.

In the use of the compound of formula I of the present invention and the pharmaceutical composition thereof in preparation a drug for treating tumors, the drug could be use to treating either human beings and other mammalians, such as other primate, bovine, equine, canine, feline, etc.

"A therapeutically effective amount" set forth in the present invention should be understood as a quantity of the compound of formula I defined above, preferably any one of the compounds shown in the formula II-VI or a mixture, or the pharmaceutically acceptable salt thereof, which could excise a notable benefit effect on a subject having tumor cells.

When the compounds of the present invention and the pharmaceutical composition thereof are used in anti-tumor treatment, they could be administrated to the subject solely, and they could also be used in combination with other anti-tumor therapies simultaneously or subsequently, such as radiation therapy.

The test results show that the compounds according to the present invention exhibit good anti-tumor effect as a prodrug in "gene-directed enzyme prodrug therapy (GDEPT)" and in "cell ablation therapy".

EXAMPLES

While the present invention will be further illustrated by the following preparation- and experiment Examples, the invention should not be limited thereto in any way.

Example 1

Preparation of
2-(1-ethyleneimine)-4-carbamoyl-3-nitropyridine
(the Compound II)

Process Procedure:

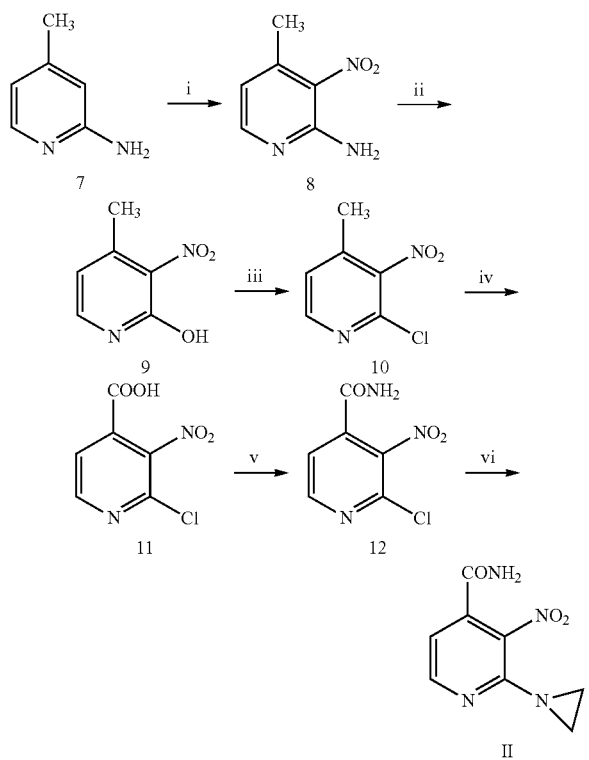

The reagents used is (i) $HNO_3/H_2SO_4$; (ii) $NaNO_2$; (iii) $POCl_3$; (iv) $K_2Cr_2O_7$; (v) $SOCl_2$, followed by $NH_4OH$; (vi) aziridine.

Synthesis of the Compound 8

A concentrated sulphuric acid (240 mL) was cooled in an ice bath, the starting material compound 7 (50 g, 0.462 mol) was slowly added and cooled to 0° C., 55 mL of a mixture in volumetric ratio of 1:1 of a concentrated sulphuric acid (98%) and a concentrated nitric acid (72%) was slowly added, then and heated slowly to 50° C., and the reaction was completed after 24 hours. The reaction solution was introduced in to 2 L ice-water, adjusted to pH=7 by adding strong aqua, and filtered. The filter cake was dried, yielding 54 g of the crude product.

The above filtrate mixture was subject to wet distillation, the resulted bright yellow liquid was subject to extraction with ethyl acetate and recrystallization in ethanol, resulting in 15 g compound 8 with a melting point of 136.1-136.4° C. (ethanol), or 135.4-135.7° C. (water) (M.P. 140° C. was reported in the reference [J. Chem. Soc. 1954, 2248-2451]). The yield is 21.2%.

Synthesis of the Compound 9

The compound 8 (11 g, 0.072 mol) was added into 150 mL of water, a concentrated sulphuric acid (11 mL) was slowly added with agitation and cooled to 0° C. in an ice bath. Sodium nitrite (9 g, 0.130 mol) was dissolved in 20 mL of water and the solution was added slowly beneath the liquid surface of the reaction solution via a long stem funnel. The reaction was run at room temperature for 2 h and was boiled up until end of the reaction marked by no further emission of a brown gas was observed. Then the reaction solution was cooled, filtered, and dried to obtain 10.8 g of the compound 9 with a yield of 97.6%. The melting point is 222.3-222.6° C. (water) (being in consistent with that disclosed in reference), 231.6-231.8° C. (ethanol).

Synthesis of the Compound 10

The compound 9 (13 g, 0.084 mol) was added into 50 mL of phosphorus oxychloride, the mixture was heated under reflux for 4 h, and distilled to remove excessive phosphorus oxychloride. The resulted product was recrystallized in 50 mL of ethanol (75%) to yield 11 g of a white solid product with yield of 75.3%. The melting point: 51.7-52.1° C. (ethanol) (M.P. 52.0-52.9° C. was reported in reference)[J.O.C., 1955, 20, 1729-1731].

Synthesis of the Compound 11

The compound 10 (11 g, 0.064 mol) was dissolved in a concentrated sulphuric acid (80 mL) with agitation, the potassium dichromate (25 g, 0.085 mol) was added slowly in batches into the system, and the reaction was run at 60° C. for 8 h. The above reaction liquid was added slowly into broken ice (250 g) and extracted three times with ethyl acetate (250 mL each). The extracts were combined and washed with a saturated aqueous solution of table salt. The solvent was evaporated and 10.5 g of the crude product was obtained with a yield of 96.3%. The crude product was recrystallized in ethanol to obtain 9.5 g of a white solid product with a yield of 87.2% and a melting point of 224.8-225.5° C. (ethanol).

Synthesis of the Compound 12

The compound 5 (3 g, 0.017 mol) was added into thionyl chloride (20 mL), two drops of DMF was added to the mixture, and then reflux was run for 2 h. The thionyl chloride was evaporated off, acetone (20 mL) was added and stirred in an ice bath, then 150 mL of aqua ammoniae was added, and the reaction was run for 1 h before being completed. The solvent was evaporated off, 30 mL water and 30 mL ethyl acetate were added to the residue, and the extraction was performed. The ethyl acetate layer was washed with a saturated aqueous solution of table salt and evaporated to dryness. The resulted product was recrystallized in ethanol (95%) to obtain 2.2 g of a white solid product, yield 73.8%. The melting point is 199.1-199.6° C. (ethanol).

Synthesis of the Compound of Formula II

The compound 6 (0.8 g, 4 mmol) was weighed and dissolved in ethyl acetate (30 mL), aziridine (0.64 g, 15 mmol) was added with agitation, and an protective argon gas was charged into the reaction system. The reaction was run for 48 h and the reaction mixture was separated by a column chromatography to obtain a light yellow product (0.32 g, 1.5 mmol). The yield is 37.5%. The melting point is 170° C. (decomposition).

$^1$H-NMR [(CD$_3$)$_2$SO]: δ 8.53 (d, 1H), 8.37 (s, 1H), 7.96 (s, 1H), 7.36 (d, 1H), 2.37 (s, 4H).

Example 2

Synthesis of the Chloride Salt of the Compound II

The compound II (1 g) was weighed, then added into a solution of excessive hydrogen chloride in methanol, and reacted at 20-25° C. for 24 h with agitation. The solvent was evaporated off, and then the chloride salt of the compound II was obtained.

Example 3

Synthesis of 2-(1-ethyleneimine)-5-carbamoyl-3-nitropyridine (Compound III)

Process Procedure:

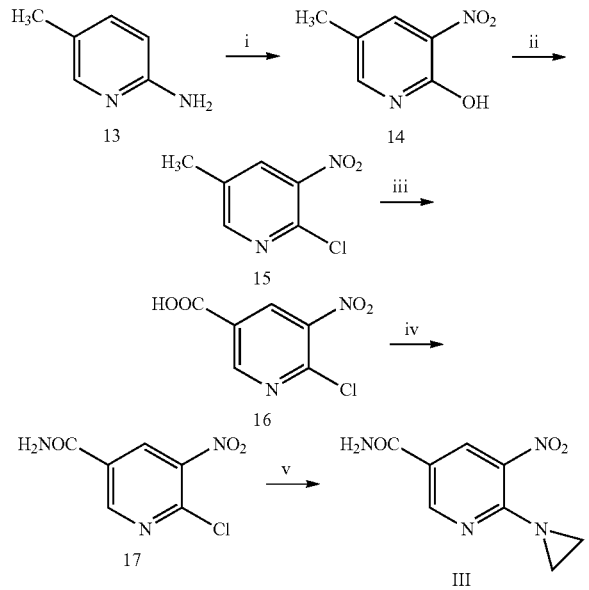

The reagents used is (i) HNO$_3$/H$_2$SO$_4$, followed by NaNO$_2$; (ii) POCl$_3$; (iii) Na$_2$Cr$_2$O$_7$; (iv) SOCl$_2$, followed by NH$_4$OH/THF; (v) aziridine.

Synthesis of the Compound 14

A concentrated sulphuric acid (25 mL) was cooled in an ice bath, the starting material compound 13 (5 g, 0.0462 mol) was slowly added and cooled to 0° C., 6 mL of a mixture in volumetric ratio of 1:1 of a concentrated sulphuric acid (98%) and a concentrated nitric acid (72%) was slowly added, and the reaction proceeded at 0-5° C. for 2 h.

The reaction liquid was introduced into 100 mL of ice-water, supplemented further with 6 g sodium nitrite, and stirred in an ice-bath for additional 4 h. A solid was precipitated and filtered. The filter cake was dried to obtain 4.4 g of the compound 14. The yield was 61.9%. The melting point is 177-178° C. (water) (M.P. 178-180° C. was reported in the reference)[J.O.C., 1944, 14, 328-332].

Synthesis of the Compound 15

The compound 14 (10 g, 0.065 mol) was added into 100 mL of phosphorus oxychloride, heated under reflux for 5 h, distilled to remove excessive phosphorus oxychloride, and poured into ice. A large amount of grey solid was precipitated and filtered to obtain 8.6 g of deep grey product with a yield of 76.8%. The melting point is 49-51° C. (water) (M.P. 46-50° C. was reported in the reference)[J.O.C., 1955, 20, 1729-1731].

Synthesis of the Compound 16

The compound 15 (3 g, 0.017 mol) was dissolved with agitation in a concentrated sulphuric acid (80 mL) in ice bath, the sodium dichromate (7.5 g, 0.025 mol) was added slowly in batches into the system, and the reaction was run at room temperature (25° C.) for 12 h. The above reaction liquid was added slowly into broken ice (50 g) and extracted with 50 mL of ethyl acetate for three times. The extracts were combined, washed with a saturated aqueous solution of table salt, dried over anhydrous magnesium sulfate, and then was subject to filtration. The solvent was evaporated off and 2.9 g of the crude product was obtained with a yield of 82.8%. The crude product was recrystallized in ethanol to obtain 2.4 g of the solid product with a yield of 68.6% and a melting point of 218° C. (ethanol)[J.O.C., 1985, 50, 1041].

Synthesis of the Compound 17

The compound 16 (4 g, 0.019 mol) was added into thionyl chloride (20 mL) and refluxed for 5 h. The thionyl chloride was evaporated off, giving an oily substance. 20 mL tetrahydrofuran was added for dissolving the oily substance, stirred in an ice bath, poured into 50 mL of aqua ammoniae, and further supplemented with 50 mL of distilled water. The reaction was run for 1 h before a large amount of yellow solid was precipitated. The precipitate was filtered and dried to obtain 3.9 g of the crude product with a yield of 97% and a melting point of 188-189° C. (water).

Synthesis of the Compound III

The compound 17 (2 g, 9.8 mmol) was weighed and dissolved in ethyl acetate (150 mL), aziridine (0.5 g, 11 mmol) was added with agitation and reacted for 30 min, then a solid was precipitated. The precipitate was filtered and dried to obtain 1.5 g of the light yellow product with a yield of 72.4%. The melting point is 150° C. (decomposition).

$^1$H-NMR [(CD$_3$)$_2$SO]: δ 8.99 (d, 1H), 8.84 (d, 1H), 8.27 (s, 1H), 7.69 (s, 1H), 2.51 (s, 4H).

Example 4

Synthesis of the Chloride Salt of the Compound III

The compound III (1 g) was weighed, added into a solution of excessive hydrogen chloride in methanol, and reacted at 20-25° C. for 24 h with agitation. The solvent was evaporated off, and then the chloride salt of the compound III was obtained.

Example 5

Synthesis of the 2-(1-ethyleneimine)-3-carbamoyl-5-nitropyridine (Compound IV)

Process Procedure:

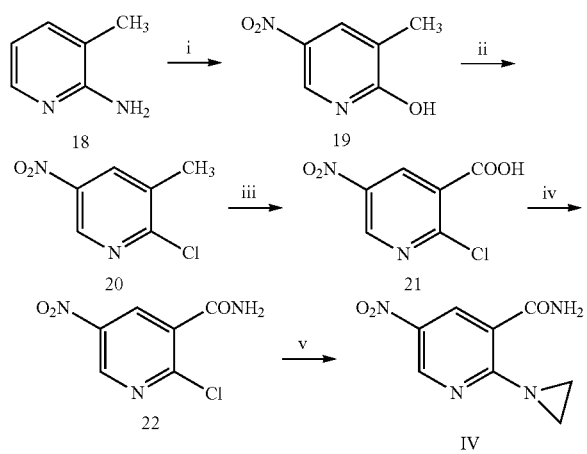

The reagents used is (i) $HNO_3/H_2SO_4$, followed by $H_2O$; (ii) $POCl_3$; (iii) $Na_2Cr_2O_7$; (iv) $SOCl_2$, followed by $NH_4OH$; (v) aziridine.

Synthesis of the Compound 19

A concentrated sulphuric acid (240 mL) was cooled in an ice bath, the starting material compound 18 (50 g, 0.462 mol) was slowly added and cooled to 0° C., 35 mL of a mixture in volumetric ratio of 1:1 of a concentrated sulphuric acid (98%) and a concentrated nitric acid (72%) was slowly added, the reaction proceeded at 25° C. for 15 h, and 35 mL of 72% $HNO_3$ was added, followed by agitation at 30° C. for 3 h. 50 mL of the reaction liquid was taken out and placed into a 1000 mL flask. 100 mL of water was added, and the solution so obtained was heated to boiling; then the rest part of the reaction liquid was added in batches to the boiling solution with 50 mL per batch. The reaction system so obtained was stirred at 100° C. for additional 1 h. After the reaction was completed, the reaction mixture was poured into 2000 g of ice, and 49.0 g of a yellow precipitate was precipitated. The melting point is 225.9-226.5° C. (water) (M.P. 228.5-229.5° C. (water) was reported in the reference)[J.O.C., 1949, 14, 328-332]. The yield was 69.2%.

Synthesis of the Compound 20

The compound 19 (16.60 g, 0.1 mol) was added into 80 mL of phosphorus oxychloride and heated under reflux for 8 h, and then distilled to remove excessive phosphorus oxychloride. The remaining solution was poured into 300 g of broken ice, and 16.18 g of a black brown precipitate was precipitated with a yield of 87.1%. The melting point is 44.5-45.8° C. (M.P. 47-48° C. was reported in the reference)[J.O.C., 1949, 14, 328-332].

Synthesis of the Compound 21

The compound 20 (8.6 g, 0.05 mol) was dissolved in a concentrated sulphuric acid (70 mL) with agitation, a sodium dichromate (20.1 g, 0.0675 mol) was added slowly in batches into the system, and the reaction was run at 30° C. for 15 h. The above reaction liquid was added slowly into broken ice (400 g) and a white precipitate was precipitated. Extraction with ethyl acetate (250 mL) was performed three times. The extracts were combined and washed with a saturated aqueous solution of table salt. The solvent was evaporated off and 8.5 g of the crude product was obtained with a yield of 84.3%. The crude product was recrystallized in ethanol to obtain 7.7 g of the compound 21 with a yield of 76.4% and a melting point of 134.2-135.3° C. (ethanol).

Synthesis of the Compound 22

The compound 21 (8.3 g, 0.04 mol) was added into thionyl chloride (80 mL) and refluxed for 3 h. The thionyl chloride was evaporated off, the acetone (240 mL) was added and stirred at 25° C., aqua ammoniae was added dropwise, and the reaction was run for 10 min before completed. The filtrate was concentrated to a quarter of the total volume, and the remaining concentrated solution was poured into 200 g of broken ice, 4.5 g of a yellow solid product was precipitated with a yield of 54.2%. The melting point is 177.3-178.2° C.

Synthesis of the Compound IV

The compound 22 (1.65 g, 8.15 mmol) was weighed and dissolved in ethyl acetate (10 mL), aziridine (0.84 mL, 16.3 mmol) was added with agitation. The reaction was run at 25° C. for 10 min and then ended. Filtration under suction was performed to obtain 1.6 g of the product with a yield of 73%. The melting point is 160° C. (decomposition).

$^1$H NMR [$(CD_3)_2SO$]: δ 9.13 (d, 1H), 8.54 (d, 1H), 8.01 (s, 1H), 7.92 (s, 1H), 2.50 (s, 4H).

Example 6

Synthesis of the Chloride Salt of the Compound IV

The compound IV (1 g) was weighed and added into a solution of excessive hydrogen chloride in methanol, and then reacted at 20-25° C. for 24 h with agitation. The solvent was evaporated off, then the chloride salt of the compound IV was obtained.

Example 7

Synthesis of the 6-(1-ethyleneimine)-2-carbamoyl-3-nitropyridine (Compound V)

Process Procedure:

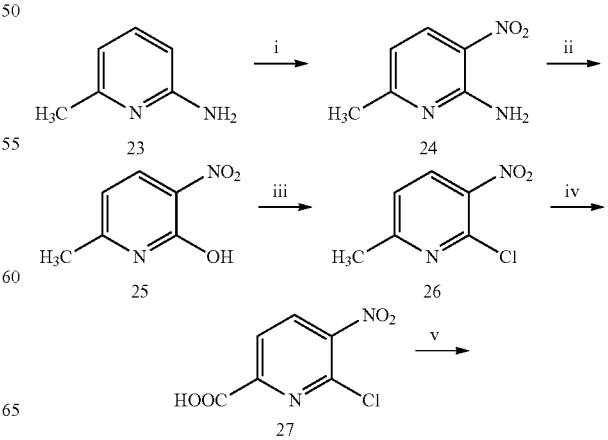

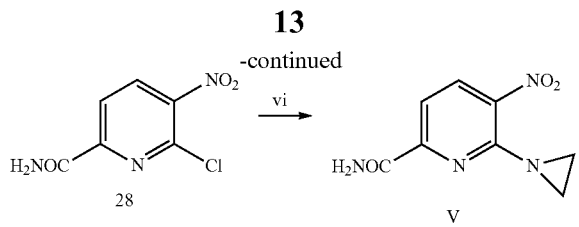

The reagents used was (i) HNO$_3$/H$_2$SO$_4$; (ii) NaNO$_2$; (iii) POCl$_3$; (iv) Na$_2$Cr$_2$O$_7$; (v) SOCl$_2$, followed by NH$_4$OH; (vi) aziridine.

Synthesis of the Compound 24

A concentrated sulphuric acid (100 mL) was cooled in an ice bath, the starting material compound 23 (30 g, 0.28 mol) was slowly added and cooled to 0° C., 42 mL of a mixture in volumetric ratio of 1:1 of a concentrated sulphuric acid (98%) and a concentrated nitric acid (72%) was slowly added, and the reaction was run at 0° C. for 1 h and left standing for 12 h. The reaction liquid was poured into 2 L of ice-water mixture, adjusted to pH=7 by adding strong aqua, and filtered. The filter cake was dried, yielding 54 g of the crude product. The above mixture was subject to wet distillation, resulting in a bright yellow liquid, and it was extracted with ethyl acetate and recrystallized in ethanol to obtain 12.5 g of the compound 24 with a melting point of 156.5-158.5° C. (ethyl acetate) and a yield of 29%.

Synthesis of the Compound 25

The compound 24 (10 g, 0.065 mol) was added into 100 mL of water, a concentrated sulphuric acid (12 mL) was slowly added with agitation and cooled to 0° C. in an ice bath. Sodium nitrite (6.9 g, 0.098 mol) was added in batches, reacted at 0° C. for 4 h, and left standing for 12 h. A large amount of yellow precipitate was precipitated, filtrated under the reduced pressure, vacuum-dried to obtain 7.7 g of a yellow product with a yield of 77%. The melting point is 216.5-218.5° C. (water).

Synthesis of the Compound 26

The compound 25 (10 g, 0.065 mol) was added into 50 mL of phosphorus oxychloride and heated under reflux for 4 h, then was subject to a distillation under a reduced pressure to remove most of phosphorus oxychloride, and the remaining part was poured into 200 g of ice-water, followed by agitation for 2 h. A large amount of the precipitate was precipitated, filtrated under a reduced pressure, and vacuum-dried to obtain 10 g of a white product with a yield of 89%. The melting point is 68.5-70.5° C. (water) [J.O.C., 1955, 20, 1729-1731].

Synthesis of the Compound 27

The compound 26 (5 g, 0.029 mol) was dissolved in a concentrated sulphuric acid (10 mL) with agitation, a sodium dichromate (11.7 g, 0.039 mol) was added slowly in batches into the system, and the reaction was run at 30° C. for 40 h. The above reaction liquid was added slowly into broken ice (300 g). A large amount of a white precipitate was precipitated, filtrated under reduced pressure, and vacuum-dried to obtain 3.8 g of a white product with a yield of 70%. The melting point is 187.5-189.5° C. (water).

Synthesis of the Compound 28

The compound 27 (3.8 g, 0.019 mol) was added into thionyl chloride (20 mL) and refluxed for 2 h. The thionyl chloride was evaporated off and followed by addition of tetrahydrofuran (15 mL) to dissolve the residue. The resulted solution was poured into 15 mL of aqua ammoniae in an ice-bath, stirred for 30 min, further supplemented with 50 mL of distilled water, and subject to further agitation. A large amount of a light-yellow precipitate was precipitated, filtrated under reduced pressure, and vacuum-dried to obtain 2.9 g of the light-yellow product with a yield of 76%. The melting point is 160.5-162.5° C. (water).

Synthesis of the Compound V

The compound 6 (1 g, 4.9 mmol) was weighed and dissolved in ethyl acetate (60 mL), 1 mL of aziridine (0.84 mL, 7.4 mmol) was added with agitation and reacted at room temperature for 4 h. A large amount of a yellow precipitate was precipitated, filtrated under reduced pressure, and vacuum-dried to obtain 1 g of a light-yellow product. The yield is 97%, and the melting point is 170° C. (decomposition).

$^1$H NMR [(CD$_3$)$_2$SO]: δ 8.55 (d, 1H), 8.17 (s, 1H), 7.88 (s, 1H), 7.79 (d, 1H), 2.51 (s, 4H).

Example 8

Synthesis of the Chloride Salt of the Compound V

The compound V (1 g) was weighed and added into a solution of excessive hydrogen chloride in methanol, and reacted at 20-25° C. for 24 h with agitation. The solvent was evaporated off, and then the chloride salt of the compound V was obtained.

Example 9

Synthesis of the 2-(1-ethyleneimine)-4-carbamoyl-5-nitropyridine (Compound VI)

Process Procedure:

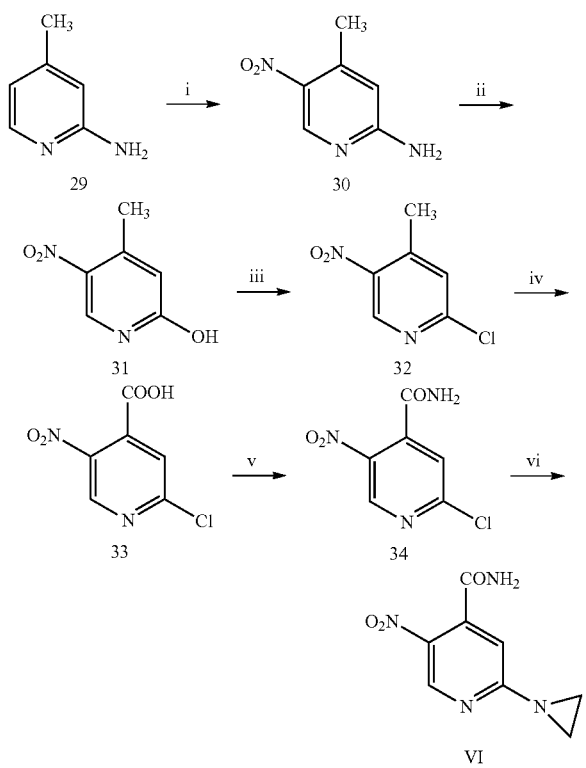

The reagents used was (i) HNO$_3$/H$_2$SO$_4$; (ii) NaNO$_2$; (iii) POCl$_3$; (iv) Na$_2$Cr$_2$O$_7$; (v) SOCl$_2$/DMF, followed by NH$_4$OH; (vi) aziridine.

Synthesis of the Compound 30

A concentrated sulphuric acid (240 mL) was cooled in an ice bath, the starting material compound 29 (50 g, 0.462 mol) was slowly added and cooled to 0° C., 55 mL of an mixture in volumetric ratio of 1:1 of a concentrated sulphuric acid (98%) and a concentrated nitric acid (72%) was slowly added and heated slowly to 50° C., and the reaction was completed after 24 hours. The reaction solution was introduced into 2 L of ice-water, followed by adjusting pH to 7 by adding strong aqua, and filtered. The filter cake was dried, yielding 54 g of the crude product.

The above mixture was subject to wet distillation to remove 4-methyl-3-nitro-2-aminopyridine, then filtered and recrystallized in ethanol (95%) to obtain 33 g of the compound 30 with a melting point of 220-222° C. (M.P. 220-222° C. was reported in the reference [J.O.C., 1955, 20, 1729-1731]). The yield was 46.6%.

Synthesis of the Compound 31

The compound 30 (17.4 g, 0.114 mol) was added into 300 mL of water, a concentrated sulphuric acid (30 mL) was slowly added with agitation and cooled to 0° C. in an ice bath. Sodium nitrite (17.5 g, 0.254 mol) was dissolved in 35 mL of water and added slowly beneath the reaction liquid surface of the reaction system via a long stem funnel. The reaction was run at room temperature for 2 h and boiled up until the reaction ends which was marked by no further brown gas was emitted. The reaction liquid was poured into broken ice, filtered, and dried to obtain 11.15 g of the compound 31 with a yield of 63.7%. The melting point is 187.3-188.9° C. (ethanol) (M.P. 186° C. was reported in the reference)[J. Chem. Soc. 1954, 2248-2451].

Synthesis of the Compound 32

The compound 31 (10.4 g, 0.067 mol) was added into 40 mL of phosphorus oxychloride and heated under reflux for 5 h, then distilled to remove excessive phosphorus oxychloride, and followed by addition of 10 mL of ethanol and then 50 mL of water. A large amount of a black solid was precipitated and filtrated to obtain 10.5 g of the crude product with a yield of 90.7%.

Synthesis of the Compound 33

The compound 32 (9.45 g, 0.055 mol) was dissolved in a concentrated sulphuric acid (80 mL) with agitation, a sodium dichromate (19.2 g, 0.065 mol) was added slowly in batches into the system, and the reaction was run at 60° C. for 6 h. The above reaction liquid was added slowly into broken ice (250 g) and extracted with ethyl acetate (300 mL) three times. The extracts were combined and washed with a saturated aqueous solution of table salt. The solvent was evaporated off and 8.65 g of the crude product was obtained with a yield of 77.6%. The crude product was recrystallized in a mixture of ethanol and petroleum ether (1:2) to obtain a white solid product with the melting point of 193.3-193.6° C. (ethanol/petroleum ether).

Synthesis of the Compound 34

The compound 33 (3 g, 0.017 mol) was added into thionyl chloride (20 mL), two drops of DMF was added to the above mixture, and then refluxed for 2 h. The thionyl chloride was evaporated off, an acetone (20 mL) was added and stirred in an ice bath, ammoniae gas was charged, and then the reaction was run for 1 h before completed. Acetone was evaporated off, 30 mL of water and 30 mL of ethyl acetate were added to the residue, and then extraction was performed. The ethyl acetate layer was washed with the saturated aqueous solution of table salt and evaporated to being dry. The resulted product was recrystallized in ethanol (95%) to obtain 0.8 g of a white solid product with a yield of 23.5%. The melting point is 193.4-193.7° C. (ethanol).

Synthesis of the Compound VI

The compound 34 (2.80 g, 14 mmol) was weighed and dissolved in ethyl acetate (150 mL), aziridine (1.8 g, 42 mmol) was added with agitation, and an protective argon gas was charged into. The reaction was run for 48 h and the reaction mixture was separated by a column chromatography to obtain a light yellow product (2.2 g, 11 mmol). The yield was 78.5%, and the melting point was 170° C. (decomposition).

$^1$H NMR [(CD$_3$)$_2$SO]: δ 8.92 (s, 1H), 8.15 (s, 1H), 7.85 (s, 1H), 7.15 (s, 1H), 2.50 (s, 4H).

Example 10

Synthesis of the Chloride Salt of the Compound VI

The compound VI (1 g) was weighed and added into a solution of excessive hydrogen chloride in methanol, and reacted at 20-25° C. for 24 h with agitation. The solvent was evaporated off, and then the chloride salt of the compound VI was obtained.

Experimental Example 1

The Anti-Tumor Tests of the Compounds II-VI Obtained in Examples of the Present Invention 1. Experimental Material 1.1 Tumor cell strain: human non-small cell lung cancer cell line A549.
1.2 Reagent system: SRB, transfection kit 2. Experimental Procedure 2.1 Technical route: The cell strains/the cypor transfected cell strains were subject to normoxic and hypoxic cultivations respectively. Then, the cell vitality was analyzed by SRB assay and IC50 values were calculated. At last, the ratio of IC50 values in normoxia and in hypoxia (hypoxic cytotoxicity ratio, HCR) was calculated.

2.2 Cell cultivation: Both the human non-small cell lung cancer cell line A549 and the cypor transfected cell strains were cultivated in F12 cultivation medium containing 10% fetal bovine serum at 37° C. and in 5% CO$_2$.

2.3 Grouping: The concentration gradient for the drug was set as $10^{-3}$, $10^{-4}$, $10^{-5}$, $10^{-6}$, and $10^{-7}$ mol/L.

2.4 Formulation of the drug: The crystallized powder of the active ingredient was dissolved in DMSO and formulated into a stock solution having a concentration which was 100 times of the maximal administrated concentration of the drug. The administrated concentrations of the drug could be prepared by directly diluting the stock solution with the corresponding serum-free cultivation medium.

2.5 Storage of the drug: the stock solution was stored at −80° C. in a refrigerator and the solutions of the drug to be administrated were prepared immediately before use.

2.6 Administration of the drug: The cell in the exponential growth phase was adjusted to a cell density of $1.0 \times 10^5$/ml and seeded into a 96-well plate at 100 µl per well. The drug was added under the normoxic and hypoxic condition respectively, according to the experimental grouping, and each of treatments using the drug lasted for 4 h.

2.7 Calculation of HCR: After treatment using the drug was completed, the treated cells were normally cultivated under a normoxic condition for 4 days and then the cell survival rate was assayed by SRB. IC$_{50}$ was calculated according to the equation of Lg $IC_{50}=\Sigma(Xi+Xi+1)(Pi+1-Pi)/2$. Hypoxia cytotoxicity ratio (HCR) was obtained through dividing $IC_{50}$ value in normoxia by $IC_{50}$ value in hypoxia. The greater the HCR value is, the stronger the hypoxic selectivity of the drug will be.

3. Statistic Method

All of the data were statistically analyzed using the software SPSS11.5, the results were expressed as a mean±standard deviation ($\overline{X}\pm SD$), the inter-group difference was tested with the program One-Way ANOVA, P<0.05 means a statistically significant difference.

4. Experimental Results

The results were shown in Table 1.

TABLE 1

Relative cell viability of the compounds II-VI for treating the tumor cells in normoxia and hypoxia

| | $WT^a$ | | | $CYPOR^c$ | | |
|---|---|---|---|---|---|---|
| | IC50 | | $HCR^b$ | IC50 | | $HCR^b$ |
| Compound | O2 | N2 | O2/N2 | O2 | N2 | O2/N2 |
| II | 198.5 ± 5.04 | 15.5 ± 2.67 | 12.8 ± 2.87 | 141.8 ± 10.06 | 2.7 ± 0.58 | 52.5 ± 3.51 |
| III | 256.7 ± 4.83 | 13.5 ± 3.20 | 19.0 ± 3.91 | 142.6 ± 9.96 | 2.3 ± 0.27 | 62.0 ± 8.32 |
| IV | 317.2 ± 2.79 | 56.6 ± 7.17 | 5.6 ± 2.73 | 198.3 ± 24.95 | 9.3 ± 3.20 | 21.3 ± 4.56 |
| V | 79.3 ± 4.77 | 9.4 ± 2.65 | 8.4 ± 3.56 | 61.0 ± 7.11 | 1.7 ± 0.38 | 35.9 ± 9.15 |
| VI | 137.4 ± 7.34 | 5.5 ± 1.60 | 25.0 ± 5.71 | 119.6 ± 6.48 | 1.1 ± 0.16 | 108.7 ± 8.88 |

[a]Wild-type
[b]HCR = $IC_{50}$ in normoxia/$IC_{50}$ in hypoxia
[c]A549 transfected with human cytochrome $P_{450}$ reducease (CYPOR).

5. Conclusion

The experimental results indicated that all of the compounds of the formula II-VI of the present invention have more intensive hypoxia-selective anti-tumor activity, for which the working mechanism may be associated with the human cytochrome $P_{450}$ reductase (CYPOR).

The invention claimed is:

1. A nitropyridinyl ethyleneimine compound as shown in the formula I or a pharmaceutically acceptable salt thereof:

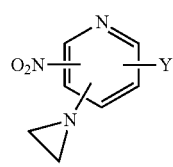

I wherein Y is —NHCOR, $CONRCO_2R^2$, CONR-morpholine, CONHR, $CONRR^2$, $CONHOR^2$, $CONHSO_2R$, $SO_2NH_2$—, $SO_2NHR$— or $SO_2NRR^2$, in which said R and $R^2$ represent independently from each other H, hydroxyl, or a $C_{1-6}$ lower alkyl group which is optionally substituted with one or more hydroxyl groups and/or one or more amino groups;

said pharmaceutically acceptable salt thereof is a salt resulted from addition with an acid or with an alkali, wherein said acid is selected from the group consisting of hydrogen chloride, sulphuric acid, phosphoric acid, acetic acid, citric acid, oxalic acid, malonic acid, salicylic acid, malic acid, fumaric acid, succinic acid, ascorbic acid, maleic acid, methane sulfonic acid or isethionic acid; said alkali is selected from the group consisting of sodium carbonate, potassium carbonate, sodium hydroxide, potassium hydroxide, ammonia, triethylamine or triethanolamine.

2. The compound or its pharmaceutically acceptable salt according to claim 1, characterized in that said compound or pharmaceutically acceptable salt thereof is one of the compounds as shown in the formula II-VI or its pharmaceutically acceptable salts:

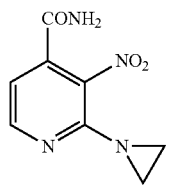

II

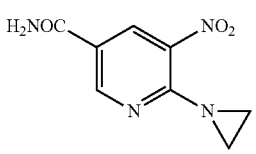

III

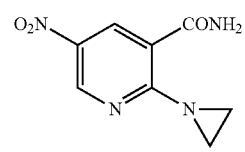

IV

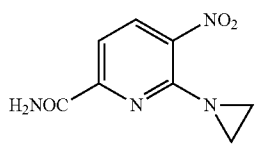

V

-continued

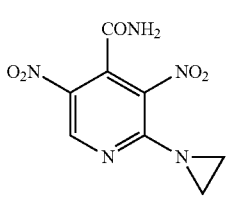

VI wherein the pharmaceutically acceptable salt thereof is the salt resulted from addition with an acid or with an alkali, said acid is selected from the group consisting of hydrogen chloride, sulphuric acid, phosphoric acid, acetic acid, citric acid, oxalic acid, malonic acid, salicylic acid, malic acid, fumaric acid, succinic acid, ascorbic acid, maleic acid, methane sulfonic acid or isethionic acid; said alkali is selected from the group consisting of sodium carbonate, potassium carbonate, sodium hydroxide, potassium hydroxide, ammonia, triethylamine or triethanolamine.

3. The compound or its pharmaceutically acceptable salt according to claim 2, wherein said compound or pharmaceutically acceptable salt thereof is compound II or its pharmaceutically acceptable salt.

4. The compound or its pharmaceutically acceptable salt according to claim 2, wherein said compound or pharmaceutically acceptable salt thereof is compound III or its pharmaceutically acceptable salt.

5. The compound or its pharmaceutically acceptable salt according to claim 2, wherein said compound or pharmaceutically acceptable salt thereof is compound IV or its pharmaceutically acceptable salt.

6. The compound or its pharmaceutically acceptable salt according to claim 2, wherein said compound or pharmaceutically acceptable salt thereof is compound V or its pharmaceutically acceptable salt.

7. The compound or its pharmaceutically acceptable salt according to claim 2, wherein said compound or pharmaceutically acceptable salt thereof is compound VI or its pharmaceutically acceptable salt.

8. A pharmaceutical composition, wherein the pharmaceutical composition comprises therapeutically effective amount of the compound or the pharmaceutically acceptable salts thereof set forth in claim 1 and pharmaceutically acceptable carrier.

* * * * *